US008785685B2

(12) United States Patent
Baumann et al.

(10) Patent No.: US 8,785,685 B2
(45) Date of Patent: Jul. 22, 2014

(54) PROCESS FOR PREPARING AMINOPOLYCARBOXYLATES PROCEEDING FROM AMINO ACIDS

(75) Inventors: Robert Baumann, Mannheim (DE); Markus Christian Biel, Mannheim (DE); Axel Franzke, Mannheim (DE); Thomas Heidenfelder, Randolph, NJ (US); Paul Klingelhoefer, Mannheim (DE); Alfred Oftring, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 290 days.

(21) Appl. No.: 13/430,105

(22) Filed: Mar. 26, 2012

(65) Prior Publication Data

US 2012/0264973 A1  Oct. 18, 2012

Related U.S. Application Data

(60) Provisional application No. 61/474,310, filed on Apr. 12, 2011.

(51) Int. Cl.
C07C 227/18 (2006.01)
C07C 227/02 (2006.01)

(52) U.S. Cl.
CPC ............ C07C 227/18 (2013.01); C07C 227/02 (2013.01)
USPC .......................................... 562/526; 562/571

(58) Field of Classification Search
CPC .................................................... C07C 227/02
USPC .............................................. 562/526, 571
See application file for complete search history.

(56) References Cited

U.S. PATENT DOCUMENTS

2011/0257431 A1 * 10/2011 Baumann et al. ............. 562/526

FOREIGN PATENT DOCUMENTS

| EP | 0 201 957 A2 | 11/1986 |
| EP | 0 506 973 A1 | 10/1992 |
| EP | 1 086 944 A2 | 3/2001 |
| WO | WO 98/50150 | 11/1998 |
| WO | WO 00/66539 | 11/2000 |
| WO | WO 03/022140 A2 | 3/2003 |
| WO | WO 03/051513 A1 | 6/2003 |
| WO | WO 2010/133617 A1 | 11/2010 |
| WO | WO 2011/045266 A1 | 4/2011 |

OTHER PUBLICATIONS

U.S. Appl. No. 13/720,027, filed Dec. 19, 2012, Bou Chedid, et al.
U.S. Appl. No. 13/463,446, filed May 3, 2012, Oftring, et al.
U.S. Appl. No. 13/321,713, filed Nov. 21, 2011, Frank Mrzena, et al.
Jochen Franz Schwieger et al., "N-Phosphorylierte Aminosäuren als potentielle Zytostatika", Cf. Arch. Pharm. (Weinheim), vol. 325, 1992, pp. 709-715.
Maurice L. Pascal, "N° 89.—Synthese de morpholones-2, des hydroxyaminoacides correspondants et de leurs chelates cuivriques, a partir des epoxydes-1,2 et des sels de sodium d'α-aminoacides", Bull. Soc. Chim. France, 1960, pp. 435-442.
U.S. Appl. No. 13/501,390, filed Apr. 11, 2012, Mrzena, et al.
U.S. Appl. No. 13/431,381, filed Mar. 27, 2012, Oftring, et al.

* cited by examiner

*Primary Examiner* — Yong Chu
(74) *Attorney, Agent, or Firm* — Oblon, Spivak, McClelland, Maier & Neustadt, L.L.P.

(57) ABSTRACT

The present invention relates to a process for preparing aminopolycarboxylates proceeding from an amino acid which, in a first process step is reacted with ethylene oxide to give an intermediate mixture comprising the corresponding dialkanolamine, and then the intermediate mixture, in a second process step is converted catalytically using a base to the corresponding aminopolycarboxylate, wherein the amino acid, before the reaction with ethylene oxide in the first process step, is supplied to a partial neutralization with 0.70 to 0.99 equivalent of base per acid group, or, in the first process step, an amino acid which has already been partly neutralized with 0.70 to 0.99 equivalent of base per acid group is used.

14 Claims, No Drawings

PROCESS FOR PREPARING AMINOPOLYCARBOXYLATES PROCEEDING FROM AMINO ACIDS

DESCRIPTION

This patent application claims the benefit of pending U.S. provisional patent application Ser. No. 61/474,310 filed on Apr. 12, 2011 incorporated in its entirety herein by reference.

The invention relates to a process for preparing aminopolycarboxylates proceeding from amino acids in two process steps, wherein, in a first process step, the amino acid is reacted with ethylene oxide to give an intermediate mixture comprising the corresponding dialkanolamine. This intermediate mixture is subsequently converted catalytically using a base to the corresponding aminopolycarboxylate.

The ethoxylation of amino acids in an aqueous medium has to date been described only for a few compounds, for example alanine, phenylalanine, aspartic acid and glutamic acid, in which cases the acid functions of the particular derivatives have been fully deprotonated, typically with sodium hydroxide solution, and hence converted to the corresponding sodium carboxylate (cf. Arch. Pharm. (Weinheim) 1992, 325, 709, Bull. Soc. Chim. France 1960, 435 and EP 1 086 944).

The oxidative dehydrogenation of amino alcohols with alkali metal hydroxides is performed typically under pressure and at temperatures of 140 to 220° C. using copper catalysts. The catalysts consist, for example, of doped or undoped Raney copper (described, for example, in WO 00/066539). The dopants used are generally one or more metals, for example Pt, Fe, Cr, Mo, V, Bi, Sn, Sb, Pb, Ge or Ag.

In other examples, copper is applied directly or via anchor metals (e.g. Os, Ir, Rh, Pt, Pd) to alkali-stable supports (e.g. WO 03/022140, WO 98/50150). Precipitated copper catalysts with further metal oxides have also been described (e.g. WO 03/051513 (Cu, Fe), EP 0 506 973 (Cu, Zr, Ca)). There have also been isolated reports about conversion over noble metal systems (e.g. EP 0 201 957).

A problem in the preparation especially of complexing agents such as MGDA (methylglycinediacetic acid) or GDA (glutamic acid diacetic acid) and salts thereof from the corresponding amino acids, such as alanine or glutamic acid, is that, in a conventional performance of the two process steps, relatively high proportions of by-products with lower efficacy or even health-damaging effects are obtained.

Purification by standard separating processes is impossible since aminopolycarboxylates are salts, have virtually no vapor pressure and therefore cannot be distilled. Spray drying can remove only components of the product mixture which have a sufficiently high vapor pressure. Most by-products, however, are likewise salts and thus cannot be removed in this way. The intermediate obtained after the first process step, the ethoxylation, is also present as a salt, which means that the purification of the intermediate mixture from the first process step is also very difficult and is afflicted with the abovementioned problems.

It was therefore an object of the invention to provide a process for preparing aminopolycarboxylates proceeding from amino acids in two process steps, i.e. an ethoxylation of the amino acid to the dialkanolamine and a catalytic oxidative dehydrogenation of the dialkanolamine to give the polycarboxylate, the use of which affords a product which has a high purity even directly, without further purification. This is equivalent to a high yield of aminopolycarboxylate over two stages proceeding from the amino acid, and this yield should be at least 91%, preferably at least 94%. A technically simple process shall be provided, which ensures the conversion of amino acids to the corresponding aminopolycarboxylates with high conversion and high selectivity, the aminopolycarboxylates which are obtained by the chemical reaction directly, without further purification, having a sufficiently high purity to be suitable as a saleable product.

This object is achieved, surprisingly, by a process for preparing aminopolycarboxylates proceeding from an amino acid which, in a
first process step is reacted with ethylene oxide to give an intermediate mixture comprising the corresponding dialkanolamine, and then the intermediate mixture, in a
second process step is converted catalytically using a base to the corresponding aminopolycarboxylate, wherein
the amino acid, before the reaction with ethylene oxide in the first process step, is supplied to a partial neutralization with 0.70 to 0.99 equivalent of base per acid group, or, in the first process step, an amino acid which has already been partly neutralized with 0.70 to 0.99 equivalent of base per acid group is used.

The present invention relates to a two-stage conversion of amino acids to the corresponding aminopolycarboxylates by the following reaction sequence:

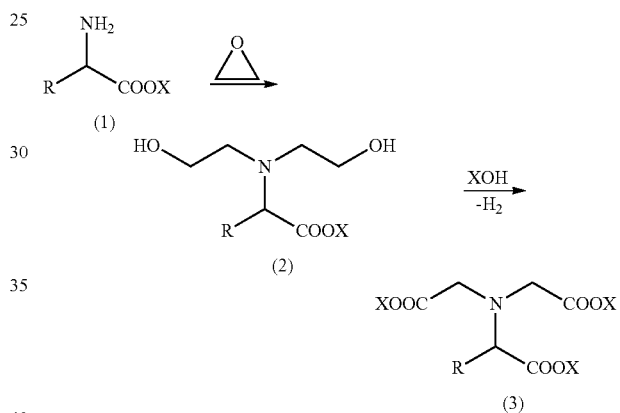

R=alkyl, alkenyl, alkynyl, aryl, aralkyl, hydroxyalkyl, hydroxyaralkyl, alkylenecarboxyl, alkylenesulfonate and
X=alkali metal and/or alkaline earth metal, and in some cases hydrogen in (1) and (2).

Non-neutralized amino acids (X=H in (1)) react only very sluggishly with ethylene oxide since the nitrogen is very substantially protonated and therefore unreactive. It is therefore customary to fully deprotonate the amino acids used as reactants in an ethoxylation (X=alkali metal and/ or alkaline earth metal in (1)). In the present process according to the invention, the amino acid is used, in contrast, in partly neutralized form (X=alkali metal and/or alkaline earth metal and in some cases hydrogen in (1)). This means that less than 1.00 equivalent of base is used per acid group. Acid groups refer in the present context to acidic functionalities such as carboxylic acid and sulfonic acid groups, but also to groups which have originated from a protonation of basic nitrogen atoms, such as ammonium salts.

The reaction in the first process step gives rise not only to the desired intermediate, the corresponding dialkanolamine, but to further main by-products which likewise derive from the amino acid: monoalkanolamine, monoether dialkanolamine which has originated from an etherification of the dialkanolamine and trialkanolammonium salt.

It has been found that the relative proportion of the secondary components obtained in the first process step depends to a high degree on the level of neutralization of the amino acid used as the reactant. In the case of use of stoichiometric amounts of base, i.e. a 100% level of neutralization of the amino acid, the above three by-products obtained in addition to the dialkanolamine form in comparable amounts. In the case of use of substoichiometric amounts of base under otherwise unchanged ethoxylation conditions, the relative proportion of the trialkanolammonium salt in the by-product spectrum rises significantly. In the case of superstoichiometric use of base, in contrast, the trialkanolammonium salt very substantially disappears, and the content of the other secondary components rises at the same time.

The monoalkanolamine and the monoether dialkanolamine by-products are unwanted since they, as complexing agents, afford substantially inactive components in the second process stage, the conversion to the particular aminopolycarboxylates. The trialkanolammonium salt, in contrast, is advantageous since it decomposes under the reaction conditions of the second process step to the desired dialkanolamine intermediate, which then forms additional product of value. This process thus leads to an increase in yield.

Aminopolycarboxylates refer in the present context to aminocarboxylates having three or four deprotonated carboxylic acid groups. Aminopolycarboxylates having three deprotonated carboxylic acid groups are especially salts of methylglycinediacetic acid; aminopolycarboxylates having four deprotonated carboxylic acid groups are especially salts of glutamic acid diacetic acid. Due to the above structure, the aminopolycarboxylates can advantageously be used as complexing agents.

The amino acid is advantageously selected from the group of the amino acids of the formula (1)

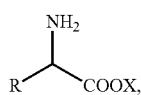

(1)

where R is an alkyl, alkenyl, alkynyl, aryl, aralkyl, hydroxyalkyl, hydroxyaralkyl, alkylenecarboxyl or alkylenesulfonate radical and X is an alkali metal, alkaline earth metal and/or hydrogen.

R is preferably a linear or branched alkyl radical which has 1 to 30 carbon atoms and may optionally also comprise rings, a linear or branched alkenyl radical which has 2 to 30 carbon atoms and may optionally also comprise rings, a linear or branched hydroxyalkyl radical having 1 to 30 carbon atoms, an alkylenecarboxylate radical having 2 to 30 carbon atoms or an alklyenesulfonate radical having 1 to 30 carbon atoms.

The amino acid is more preferably selected from the group comprising alanine, glutamic acid and serine.

When the amino acid of the formula (1) is a chiral compound having at least one asymmetric carbon atom, this compound can be used in enantiomerically pure, scalemic or else racemic form.

The bases used for the partial neutralization of the amino acid before the reaction with ethylene oxide in the first process step may advantageously be hydroxides and/or carbonates of alkali metals and/or alkaline earth metals, individually or as a mixture thereof.

It is advantageous to use sodium hydroxide or potassium hydroxide.

Particularly advantageously, sodium hydroxide or potassium hydroxide is used in aqueous solution, especially in approx. 50% by mass aqueous solution.

Sodium hydroxide or potassium hydroxide can advantageously also be used in solid form.

Advantageously, the amino acid is deprotonated with 0.85 to 0.99 equivalent of base per acid group.

With regard to the amount of ethylene oxide used, preference is given to a process in which 1.80 to 2.60, more preferably 2.00 to 2.35, equivalents of ethylene oxide are used per amino group.

There are also preferred variants with regard to the reaction temperature in the first stage. For instance, preference is given to a process in which the reaction temperature is in the range from 30 to 100° C., preferably in the range from 60 to 90° C. The reaction temperature in the first process stage varies during the metered addition of the ethylene oxide preferably by less than 40° C., more preferably by less than 25° C.

The process can be performed as a batchwise, semibatchwise or continuous process. A process in which (at least) one reactor selected from the group comprising stirred tank reactor, loop reactor and tubular reactor is used is particularly preferred.

This is possible using various reactor models, such as stirred tank reactors of various designs, loop reactors configured as a gas circulation reactor, immersed jet reactor, jet nozzle reactor or high-loading packed column, or tubular reactors, which are operated without or with a gas phase.

A process in which the reactor consists essentially of a material with a thermal conductivity coefficient of greater than 5 W/K*m is particularly suitable. "Essentially" means that more than 50%, preferably more than 80% and more preferably more than 90% of the reactor material consists of a material with a corresponding thermal conductivity coefficient.

Particularly suitable materials for this purpose are found to be materials such as 1.4541 (V2A steel), 1.4571 (V4A steel), 2.4610 (HC4 steel) with a thermal conductivity coefficient greater than 5 W/K*m, in order to enable efficient heat removal in the industrial process.

Likewise preferred is a process in which the solvent of the first stage is selected from protic solvents such as water, alcohols, preferably short-chain alcohols, and especially methanol, ethanol, 2-propanol, and/or polar aprotic solvents such as dimethyl sulfoxide, dimethylformamide or N-methylpyrrolidone. Particular preference is given to the use of water as the solvent.

The concentration of the free amino acid and salts thereof in the reaction medium before the reaction starts as a result of commencement of the ethylene oxide metering can be varied over wide ranges. It is preferably 5 to 80% by mass, more preferably 30 to 70% by mass.

A particularly preferred embodiment of the process consists in partly neutralizing the amino acid to which some or all of the solvent has been added with the required amount of base in a separate reactor or the reactor used for the actual ethoxylation, before ethylene oxide metering is commenced.

This use of two reactors or vessels in series is advantageous especially in a continuous mode of operation, in order to separate the partial neutralization from the first process step, the ethoxylation. In a batchwise mode of operation, in contrast, it is possible to add the base for the partial neutralization and the ethylene oxide for the reaction in the first process step successively in the same reactor or vessel.

A process in which the intermediate mixture which comprises the dialkanolamine and is formed in the first stage is directly dehydrogenated constitutes a further preferred embodiment. A direct dehydrogenation means that there is no apparatus removal, based on different boiling points, of substances having boiling points greater than 200° C. (at standard pressure) between the first and second stages. This is simpler in apparatus terms and thus dispenses with one operation with comparably good end product quality.

The dehydrogenation is effected using a base from the group comprising the alkali metal and alkaline earth metal hydroxides, preferably sodium hydroxide or potassium hydroxide, particular preference being given to sodium hydroxide. The temperature in the second stage is typically in the range from 140 to 240° C., preferably in the range from 150 to 210° C. and more preferably in the range from 160 to 200° C. The pressure is typically in the range from standard pressure to 100 bar, preferably from 5 to 50 bar and more preferably in the range from 8 to 20 bar.

A process in which the dehydrogenation is performed in the presence of a catalyst whose main and secondary constituents are selected from groups 4 to 12 of the periodic table is particularly preferred; very particular preference is given to a process in which the dehydrogenation is performed in the presence of a catalyst comprising (at least) one metal selected from the group comprising Cu, Fe, Co, Ni, Zr, Hf, Ag, Pd and Pt.

The catalyst can be used, for example, in the form of powder or shaped bodies (e.g. extrudates, tablets), and in the form of an unsupported or supported catalyst, and may consist of metals and metal oxides.

A process in which the content of nitrilotriacetic acid (NTA) or salts thereof in the direct product of the second stage is less than 1% by mass based on the main product forms a further part of the subject matter of the present invention.

The direct product of the second stage is understood to mean the reaction discharge as obtained in the oxidative dehydrogenation. Thereafter, in the case of a suspension mode, the catalyst can be sedimented and/or filtered off. In addition, it is subsequently possible to establish a desired water content and/or to conduct bleaching, for example with hydrogen peroxide or UV light.

In addition to the salts (aminopolycarboxylates) themselves, the corresponding aminopolycarboxylic acids are also obtainable after acidification.

Particular preference is given to a process in which the end product too, apart from the aforementioned measures, is not purified any further, but is used directly in the corresponding applications, for example as an additive for industrial cleaning formulations for hard surfaces of metal, plastic, coating material or glass, in alkaline cleaning formulations for the drinks and foods industry, especially for bottle cleaning in the drinks industry and for apparatus cleaning in dairies, in breweries, in the preserves industry, in the bakery industry, in the sugar industry, in the fat-processing industry and in the meat-processing industry, in dishware cleaning formulations, especially in phosphate-free compositions for machine dishwashing in machine dishwashers in the household or in commercial premises, for example large kitchens or restaurants, in bleaching baths in the paper industry, in photographic bleaching and bleach fixing baths, in pretreatment and bleaching in the textile industry, in electrolytic baths for masking of contaminating heavy metal cations, and also in the field of plant foods for remedying heavy metal deficits as copper, iron, manganese and/or zinc complexes. In principle, use is advantageous wherever precipitations of calcium, magnesium or heavy metal salts disrupt industrial processes and should therefore be prevented (prevention of deposits and encrustations in tanks, pipelines, spray nozzles or generally on smooth surfaces). The aminopolycarboxylates can also be used for stabilization of phosphates in alkaline degreasing baths and for prevention of the precipitation of lime soaps, in order thus to prevent the tarnishing of non-iron surfaces and to prolong the service life of alkaline cleaning baths. In addition, they find use in pulverulent or liquid detergent formulations for textile washing as builders and preservatives. In soaps, they prevent metal-catalyzed oxidative decompositions, and also in pharmaceuticals, cosmetics and foods.

The present invention is illustrated in detail hereinafter by nonlimiting examples:

EXAMPLE 1

The following describes partial neutralization of the amino acid alanine according to the invention with 0.98 equivalent of base per acid group:

267 g (3.00 mol) of alanine were suspended in 161 g of water, and 238 g (2.94 mol), i.e. 0.98 equivalent of base per acid group, of 49.4% by mass sodium hydroxide solution were added. The resulting mixture was introduced into a 2.5 L autoclave (material: 1.4571) and, after appropriate inertization, pressurized with 20 bar of nitrogen. Subsequently, 291 g (6.60 mol) of ethylene oxide were metered in at 40-50° C. within 6 h and stirring was continued at this temperature for a further 5 h. After the removal of the unconverted residues of ethylene oxide, the autoclave was emptied. In this way, 934 g of aqueous reaction discharge were obtained as a clear, colorless, viscous solution.

324 g (1.04 mol based on alanine) of this intermediate were initially charged with 199 g (2.49 mol) of 50% by mass sodium hydroxide solution, 49 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 16 h. The stirrer speed over the entire experimental duration was 500 rpm. The hydrogen formed was removed continuously by means of a valve which regulates the pressure at 10 bar. After the end of the experiment, the reactor was purged with nitrogen at room temperature, and the reaction discharge was diluted with 406 g of water and then emptied. The product was obtained as a clear, colorless, viscous solution. By means of HPLC, a yield (=selectivity*conversion) of methylglycine-N,N-diacetic acid trisodium salt (MGDA-Na$_3$) of 94.0% of theory based on alanine used was determined. The yield of the corresponding monoether polycarboxylate was less than 3% of theory based on alanine used.

The reaction to give the product of value proceeded with high selectivity and high conversion, with a simultaneously very low content of unwanted monoether polycarboxylate. Therefore, no purification of the reaction product was required.

COMPARATIVE EXAMPLE 1

The following describes complete neutralization of the amino acid alanine according to the prior art with 1.00 equivalent of base per acid group:

178 g (2.00 mol) of alanine were suspended in 106 g of water, and 160 g (2.00 mol), i.e. 1.00 equivalent of base per acid group, of 50.0% by mass sodium hydroxide solution were added. The resulting mixture was introduced into a 2.5 L autoclave (material: 1.4571) and, after appropriate inertization, pressurized with 2 bar of nitrogen. Subsequently, 189 g (4.30 mol) of ethylene oxide were metered in at 40-50° C. within 4 h and stirring was continued at this temperature for a further 5 h. After the removal of the unconverted residues of ethylene oxide, the autoclave was emptied. In this way, 624 g of aqueous reaction discharge were obtained as a clear, colorless, viscous solution.

324 g (1.04 mol based on alanine) of this intermediate were initially charged with 208 g (2.60 mol) of 50% by mass sodium hydroxide solution, 39 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 16 h. The stirrer speed over the entire experimental duration was 500 rpm. The hydrogen formed was removed continuously by means of a valve which regulates the pressure at 10 bar. After the end of the experiment, the reactor was purged with nitrogen at room temperature, and the reaction discharge was diluted with 423 g of water and then emptied. The product was obtained as a clear, colorless, viscous solution. By means of HPLC, a yield (=selectivity*conversion) of methylglycine-N,N-diacetic acid trisodium salt (MGDA-$Na_3$) of 89.9% of theory based on alanine used was determined. The yield of the corresponding monoether polycarboxylate was 6% of theory based on alanine used.

The reaction to give the product of value proceeded with high conversion but reduced selectivity, with a simultaneously increased level of unwanted monoether polycarboxylate. The reaction product thus has a reduced purity and has to be correspondingly purified.

COMPARATIVE EXAMPLE 2

The following describes complete neutralization of the amino acid alanine with a slight excess of 1.10 equivalents of base per acid group:

267 g (3.00 mol) of alanine were suspended in 132 g of water, and 267 g (3.30 mol), i.e. 1.10 equivalents of base per acid group, of 49.4% by mass sodium hydroxide solution were added. The resulting mixture was introduced into a 2.5 L autoclave (material: 1.4571) and, after appropriate inertization, pressurized with 20 bar of nitrogen. Subsequently, 291 g (6.60 mol) of ethylene oxide were metered in at 40-50° C. within 6 h and stirring was continued at this temperature for a further 5 h. After the removal of the unconverted residues of ethylene oxide, the autoclave was emptied. In this way, 940 g of aqueous reaction discharge were obtained as a clear, colorless, viscous solution.

326 g (1.04 mol based on alanine) of this intermediate were initially charged with 190 g (2.37 mol) of 50% by mass sodium hydroxide solution, 55 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 16 h. The stirrer speed over the entire experimental duration was 500 rpm. The hydrogen formed was removed continuously by means of a valve which regulates the pressure at 10 bar. After the end of the experiment, the reactor was purged with nitrogen at room temperature, and the reaction discharge was diluted with 481 g of water and then emptied. The product was obtained as a clear, colorless, viscous solution. By means of HPLC, a yield (=selectivity*conversion) of methylglycine-N,N-diacetic acid trisodium salt (MGDA-$Na_3$) of 71.5% of theory based on alanine used was determined. The yield of the corresponding monoether polycarboxylate was 11% of theory based on alanine used.

The reaction to give the product of value proceeded with high conversion but greatly reduced selectivity, with a simultaneously distinctly increased level of unwanted monoether polycarboxylate. The reaction product thus has a considerably reduced purity and has to be purified correspondingly.

EXAMPLE 2

The following describes partial neutralization of the amino acid alanine according to the invention with likewise 0.98 equivalent of base per acid group, but the oxidative dehydrogenation was performed with a shortened reaction time compared to Example 1:

324 g (1.04 mol based on alanine) of the intermediate from Example 1 were initially charged with 200 g (2.50 mol) of 50% by mass sodium hydroxide solution, 49 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 8 h. The stirrer speed over the entire experimental duration was 500 rpm. The hydrogen formed was removed continuously by means of a valve which regulates the pressure at 10 bar.

After the end of the experiment, the reactor was purged with nitrogen at room temperature, and the reaction discharge was diluted with 416 g of water and then emptied. The product was obtained as a clear, colorless, viscous solution. By means of HPLC, a yield (=selectivity*conversion) of methylglycine-N,N-diacetic acid trisodium salt (MGDA-$Na_3$) of 92.5% of theory based on alanine used was determined. The yield of the corresponding monoether polycarboxylate was less than 3% of theory based on alanine used.

The reaction to give the product of value proceeded again with high selectivity and high conversion, with a simultaneously very low content of unwanted monoether polycarboxylate. Purification of the reaction product was therefore again unnecessary.

EXAMPLE 3

The following describes partial neutralization of the amino acid alanine according to the invention with only 0.90 equivalent of base per acid group:

178 g (2.00 mol) of alanine were suspended in 120 g of water, and 146 g (1.80 mol), i.e. 0.90 equivalent of base per acid group, of 49.4% by mass sodium hydroxide solution were added. The resulting mixture was introduced into a 2.5 L autoclave (material: 1.4571) and, after appropriate inertization, pressurized with 20 bar of nitrogen. Subsequently, 194 g (4.40 mol) of ethylene oxide were metered in at 40-50° C. within 4 h and stirring was continued at this temperature for a further 5 h. After the removal of the unconverted residues of ethylene oxide, the autoclave was emptied. In this way, 619 g of aqueous reaction discharge were obtained as a clear, colorless, viscous solution.

322 g (1.04 mol based on alanine) of this intermediate were initially charged with 217 g (2.71 mol) of 50% by mass sodium hydroxide solution, 38 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 16 h. The stirrer speed over the entire experimental duration was 500 rpm. The hydrogen formed was removed continuously by means of a valve which regulates the pressure at 10 bar. After the end of the experiment, the reactor was purged with nitrogen at room temperature, and the reaction discharge was diluted with 425 g of water and then emptied. The product was obtained as a. clear, colorless, viscous solution. By means of HPLC, a yield (=selectivity*conversion) of methylglycine-N,N-diacetic acid trisodium salt (MGDA-Na$_3$) of 94.1% of theory based on alanine used was determined. The yield of the corresponding monoether polycarboxylate was less than 3% of theory based on alanine used.

The reaction to give the product of value proceeded again with high selectivity and high conversion, with a simultaneously very low content of unwanted monoether polycarboxylate. Purification of the reaction product was therefore again unnecessary.

EXAMPLE 4

The following describes partial neutralization of the amino acid alanine according to the invention with likewise only 0.90 equivalent of base per acid group, but the ethoxylation was performed under altered process parameters compared to Example 3:

178 g (2.00 mol) of alanine were suspended in 46 g of water, and 146 g (1.80 mol), i.e. 0.90 equivalent of base per acid group, of 49.4% by mass sodium hydroxide solution were added. The resulting mixture was introduced into a 2.5 L autoclave (material: 1.4571) and, after appropriate inertization, pressurized with 20 bar of nitrogen. Subsequently, 203 g (4.60 mol) of ethylene oxide were metered in at 80-85° C. within 2 h and stirring was continued at this temperature for a further 2 h. After the removal of the unconverted residues of ethylene oxide, the autoclave was emptied. In this way, 527 g of aqueous reaction discharge were obtained as a clear, colorless, viscous solution.

274 g (1.04 mol based on alanine) of this intermediate were initially charged with 217 g (2.71 mol) of 50% by mass sodium hydroxide solution, 81 g of water and 45 g of Raney copper (from Evonik Degussa GmbH) in a 1.7 L autoclave (material: 2.4610). The reactor was closed, pressurized with 5 bar of nitrogen and then heated to 190° C. within 2.25 h. This temperature was maintained for 16 h. The stirrer speed over the entire experimental duration was 500 rpm. The hydrogen formed was removed continuously by means of a valve which regulates the pressure at 10 bar. After the end of the experiment, the reactor was purged with nitrogen at room temperature, and the reaction discharge was diluted with 403 g of water and then emptied. The product was obtained as a clear, colorless, viscous solution. By means of HPLC, a yield (=selectivity*conversion) of methylglycine-N,N-diacetic acid trisodium salt (MGDA-Na$_3$) of 94.2% of theory based on alanine used was determined. The yield of the corresponding monoether polycarboxylate was less than 3% of theory based on alanine used.

The reaction to give the product of value proceeded again with high selectivity and high conversion, with a simultaneously very low content of unwanted monoether polycarboxylate. Purification of the reaction product was therefore again unnecessary.

The invention claimed is:

1. A process for preparing an aminopolycarboxylate from an amino acid, the process comprising:
    reacting the amino acid with ethylene oxide to obtain an intermediate mixture comprising dialkanolamine, and
    catalytically converting the intermediate mixture with a base to an aminopolycarboxylate,
    wherein the amino acid, before the reacting is partially neutralized with from 0.70 to 0.99 equivalent of base per acid group, or, in the reacting, an amino acid which has already been partially neutralized with from 0.70 to 0.99 equivalent of base per acid group is provided.

2. The process according to claim 1,
wherein the amino acid is of formula:

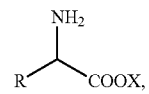

wherein R is an alkyl, alkenyl, alkynyl, aryl, aralkyl, hydroxyalkyl, hydroxyaralkyl, alkylenecarboxyl or alkylenesulfonate radical and
X is an alkali metal, alkaline earth metal, hydrogen or any combination thereof.

3. The process according to claim 2,
wherein R is a linear or branched alkyl radical having 1 to 30 carbon atoms and optionally also comprises rings, a linear or branched alkenyl radical having 2 to 30 carbon atoms and optionally also comprises rings, a linear or branched hydroxyalkyl radical having 1 to 30 carbon atoms, an alkylenecarboxylate radical having 2 to 30 carbon atoms or an alklyenesulfonate radical having 1 to 30 carbon atoms.

4. The process according to claim 3,
wherein the amino acid is selected from the group consisting of alanine, glutamic acid, and serine.

5. The process according to claim 1,
wherein the base is a hydroxide, carbonate, or both hydroxide and carbonate of an alkali metal, alkaline earth metal, or mixture thereof.

6. The process according to claim 5,
wherein the base is sodium hydroxide or potassium hydroxide.

7. The process according to claim 6,
wherein the sodium hydroxide or potassium hydroxide is contacted in an aqueous solution.

8. The process according to claim 1,
wherein the reacting is performed at a reaction temperature of from 30 to 100° C.

9. The process according to claim 1,
wherein the reacting is performed so that a reaction temperature during the reacting varies by less than 40° C.

10. The process according to claim 1,
wherein the reacting is performed in the presence of a protic, polar aprotic solvent, or both.

11. The process according to claim 7,
wherein an amount of the sodium hydroxide or potassium hydroxide is 50% by mass aqueous solution.

12. The process according to claim 8,
wherein the reacting is performed at a reaction temperature of from 60 to 90° C.

13. The process according to claim 9,
wherein the reacting is performed so that the reaction temperature during the reacting varies by less than 25° C.

14. The process according to claim 10, wherein the reacting is performed in the presence of water.

* * * * *